United States Patent
Chenvainu et al.

(10) Patent No.: US 8,239,995 B2
(45) Date of Patent: Aug. 14, 2012

(54) TOOTHBRUSH WITH MULTIPLE BRISTLES STATES

(75) Inventors: Alexander Timothy Chenvainu, Sudbury, MA (US); Marc Phillip Ortins, Reading, MA (US); Karen Lynn Claire-Zimmet, Waltham, MA (US)

(73) Assignee: The Gillette Company, Boston, MA (US)

( * ) Notice: Subject to any disclaimer, the term of this patent is extended or adjusted under 35 U.S.C. 154(b) by 1247 days.

(21) Appl. No.: 11/899,655

(22) Filed: Sep. 7, 2007

(65) Prior Publication Data

US 2008/0066251 A1    Mar. 20, 2008

Related U.S. Application Data

(60) Provisional application No. 60/843,281, filed on Sep. 8, 2006, provisional application No. 60/880,684, filed on Jan. 16, 2007.

(51) Int. Cl.
*A46B 9/04*    (2006.01)

(52) U.S. Cl. .............. 15/167.1; 15/207.2; 15/22.1
(58) Field of Classification Search ............... 15/167.1, 15/110, 207.2, 22.1, 22.2, 28
See application file for complete search history.

(56) References Cited

U.S. PATENT DOCUMENTS 5,350,248 A * 9/1994 Chen ........................ 401/195
6,938,294 B2 * 9/2005 Fattori et al. ............... 15/22.2

* cited by examiner

*Primary Examiner* — Shay Karls
(74) *Attorney, Agent, or Firm* — George H. Leal; James E. Oehlenschlager; Vladimir Vitenberg

(57) ABSTRACT

An oral hygiene device includes a head, a first bristle field, and a second bristle field. The head includes a first head portion and a second head portion. The first bristle field extends from the first head portion. The second bristle field extends from the second head portion. The first bristle field and second bristle field are controllably movable between a first configuration for providing a first cleaning operation and a second configuration for providing a second cleaning operation.

17 Claims, 13 Drawing Sheets

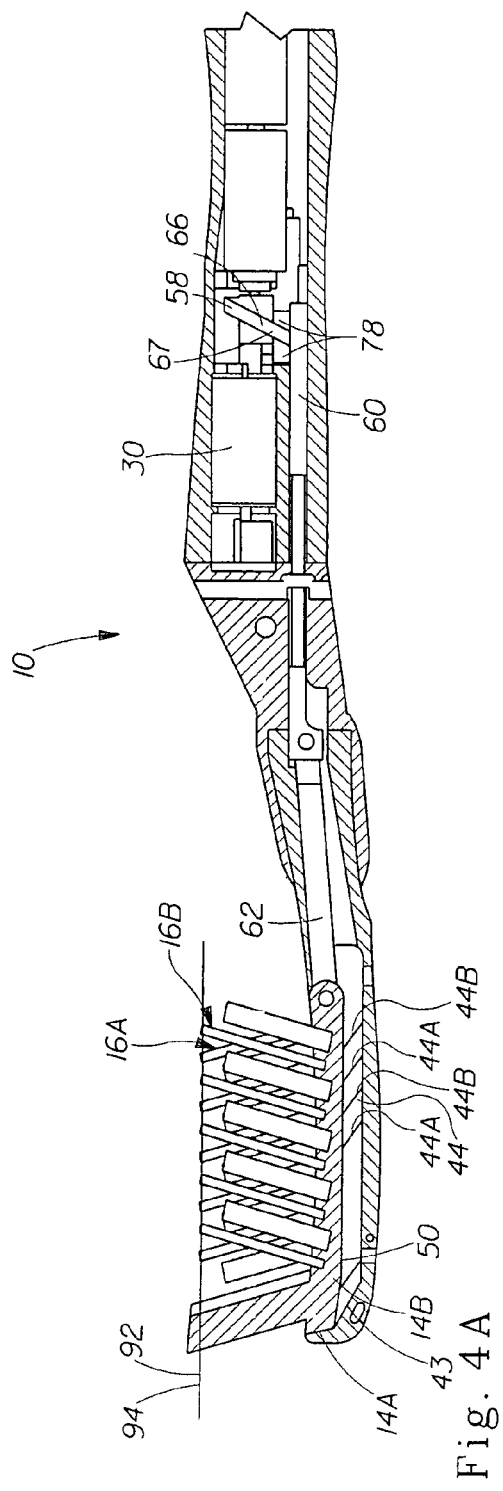
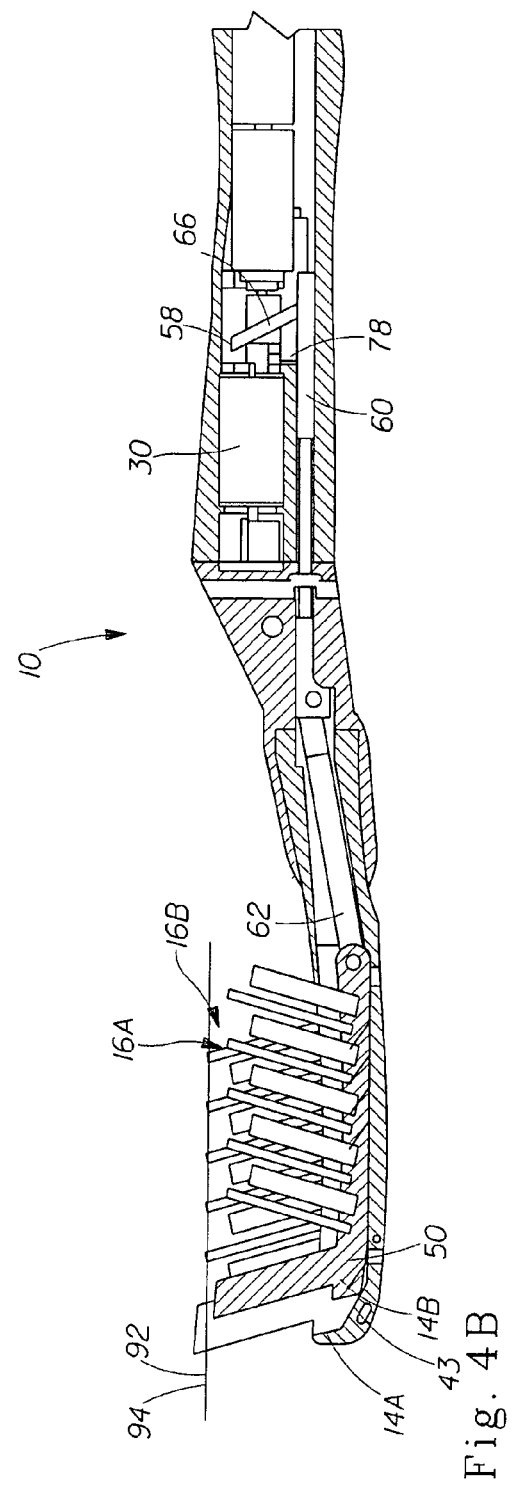
Fig. 4A
Fig. 4B

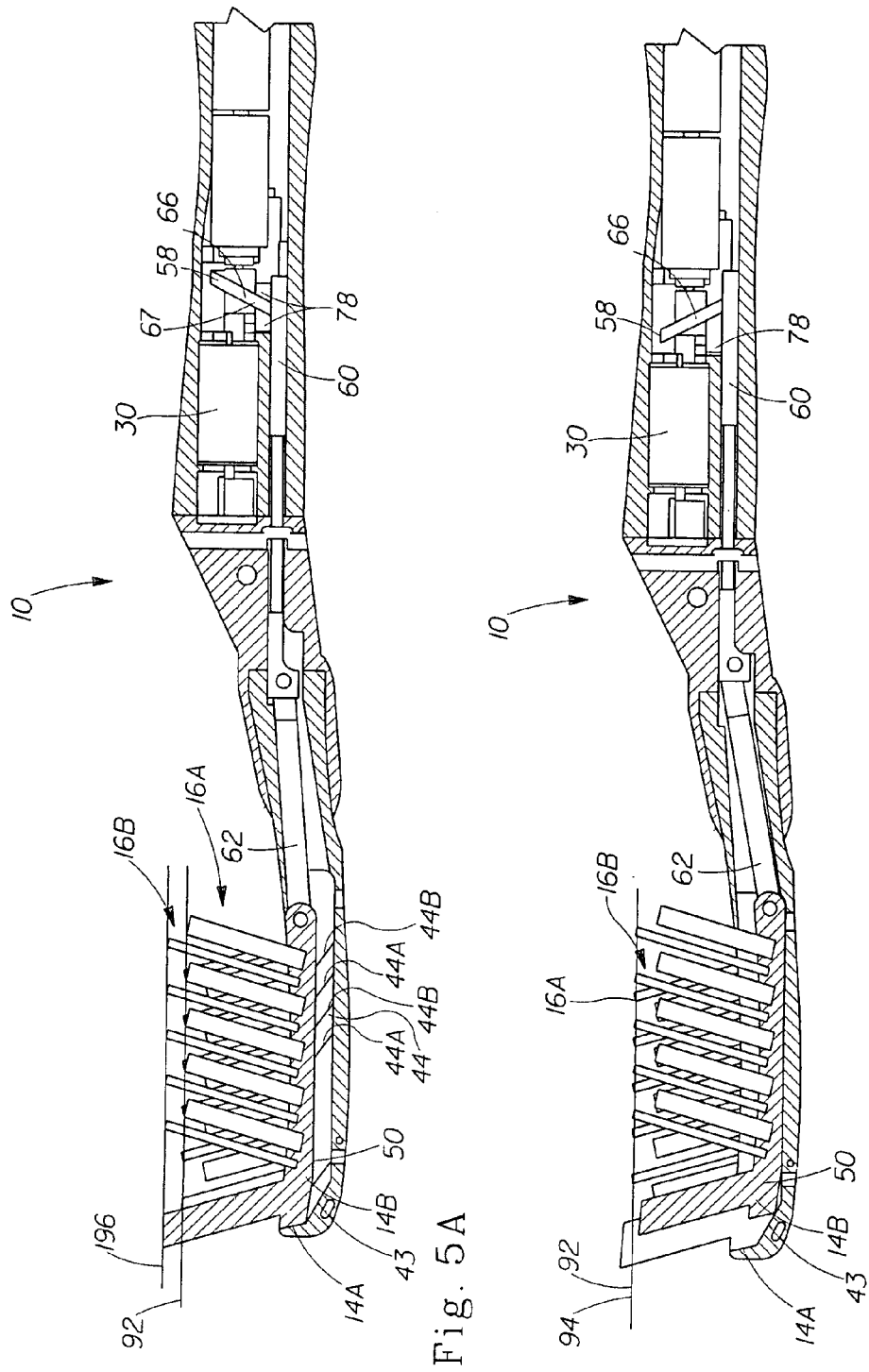

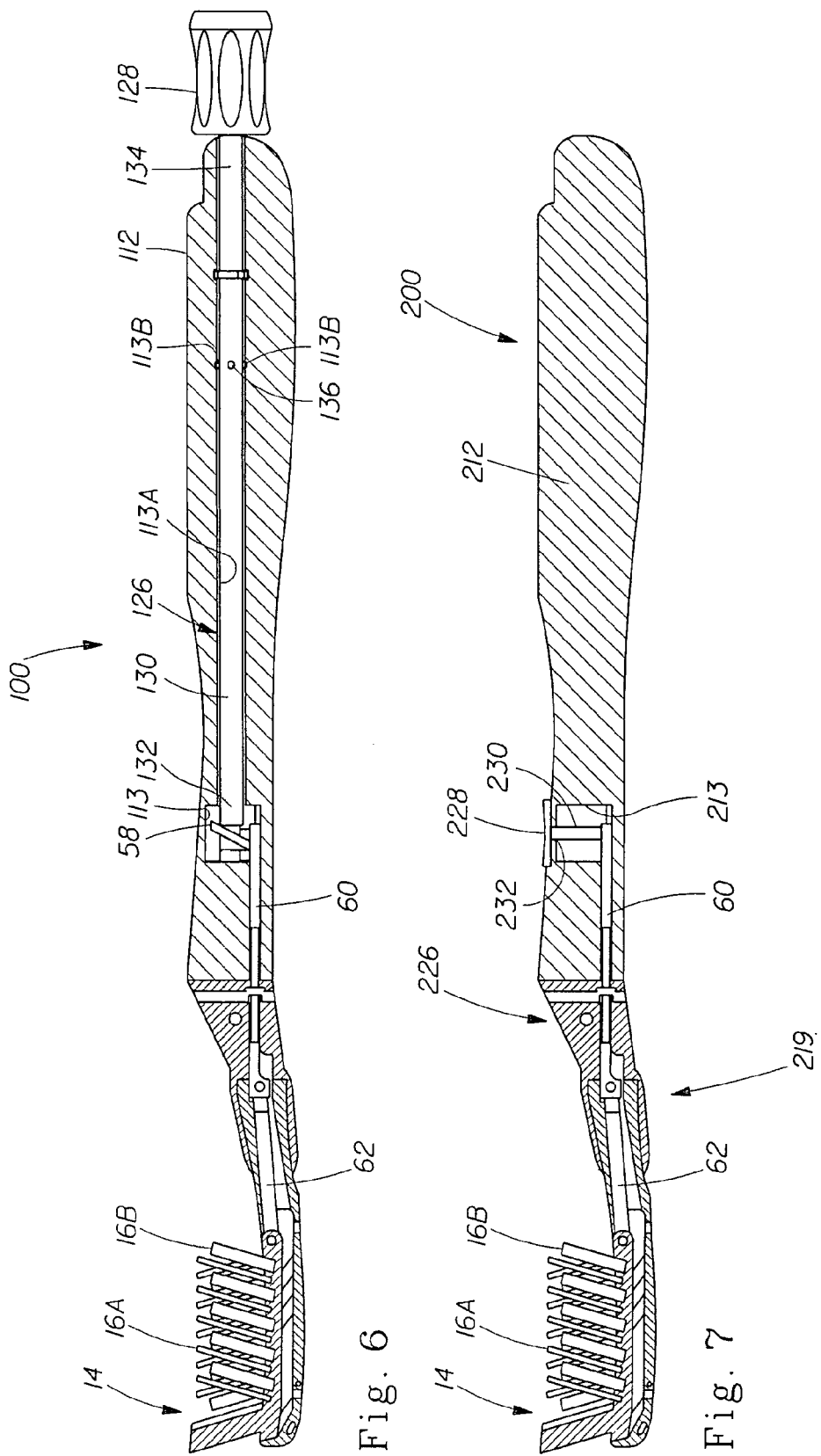

TOOTHBRUSH WITH MULTIPLE BRISTLES STATES

CROSS REFERENCE

This application claims the benefit of U.S. Application Ser. No. 60/843,281 filed on Sep. 8, 2006 and claims the benefit of U.S. Application Ser. No. 60/880,684 filed on Jan. 16, 2007, each of which is incorporated herein by reference.

FIELD OF THE DISCLOSURE

The present disclosure relates generally to a toothbrush and, more particularly, to a toothbrush having bristles that are moveable between multiple states.

BACKGROUND

Toothbrush development has historically been focused on the development of manual and powered toothbrushes. Manual toothbrushes tend to include a fixed bristle pattern for cleaning a user's teeth. Recent advancements in manual toothbrushes include angled, multi-level bristles, and pivoting tufts or cleaning elements. The primary success of these designs lies in their ability to surface clean including the removal of surface plaque. In order to use a manual toothbrush, a user must manually manipulate the brush to provide a back-and-forth and/or circular cleaning motion. Typical powered toothbrushes operate similarly, with the exception that a power source provides the primary cleaning motion. For example, in one conventional powered toothbrush, a power source spins a brush head with generally uniform bristle tufts. In another conventional powered toothbrush, a power source vibrates a brush head at a high frequency. The power source may thereby replace the need for a user to manually manipulate the toothbrush in the back-and-forth and/or circular cleaning motion.

One shortcoming of these conventional manual and powered toothbrushes is that they merely provide for surface cleaning. These conventional manual and powered toothbrushes may not provide sufficient interproximal cleaning. Unfortunately, this may lead to less than ideal oral care.

SUMMARY

One aspect of the present disclosure provides an oral hygiene device having a head, a first bristle field and a second bristle field. The head includes a first head portion and a second head portion. The first bristle field extends from the first head portion. The second bristle field extends from the second head portion. The first bristle field and second bristle field are controllably movable between a first configuration for providing a first cleaning operation and a second configuration for providing a second cleaning operation.

According to another aspect, the first bristle field and the second bristle field terminate in a common plane when in the first configuration and the first bristle field extends beyond the second bristle field when in the second configuration.

According to another aspect, the first bristle field terminates in a first plane and the second bristle field terminates in a second plane when in the first configuration and wherein the second bristle field terminates in a third plane when in the second configuration.

According to another aspect, the second plane is disposed between about 0 millimeters and about 2 millimeters from the third plane.

According to another aspect, the toothbrush further includes a manual actuator for controllably moving the first and second bristle fields between the first and second configurations.

According to another aspect, the toothbrush further includes a powered actuator for controllably moving the first and second bristle fields between the first and second configurations.

According to yet another aspect, the powered actuator cycles the first and second bristle fields between the first and second configurations, and wherein a time period between cycles is at least about 0.5 seconds.

According to still another aspect, the time period between cycles is between about 0.5 seconds and about 3 seconds.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 4A is a partial cross-sectional side view of the toothbrush of FIGS. 1-3 having bristles arranged in a first configuration;

FIG. 4B is a partial cross-sectional side view of the toothbrush of FIGS. 1-3 having bristles arranged in a second configuration;

FIG. 5A is a partial cross-sectional side view showing another embodiment of the toothbrush of FIGS. 1-3 having bristles arranged in a second configuration;

FIG. 5B is a partial cross-sectional side view showing another embodiment of the toothbrush of FIGS. 1-3 having bristles arranged in a first configuration;

FIG. 6 is a cross-sectional side view of one alternate form of a toothbrush constructed according to the principles of the present disclosure;

FIG. 7 is a cross-sectional side view of another alternate form of a toothbrush constructed according to the principles of the present disclosure;

DETAILED DESCRIPTION

Figure 1:
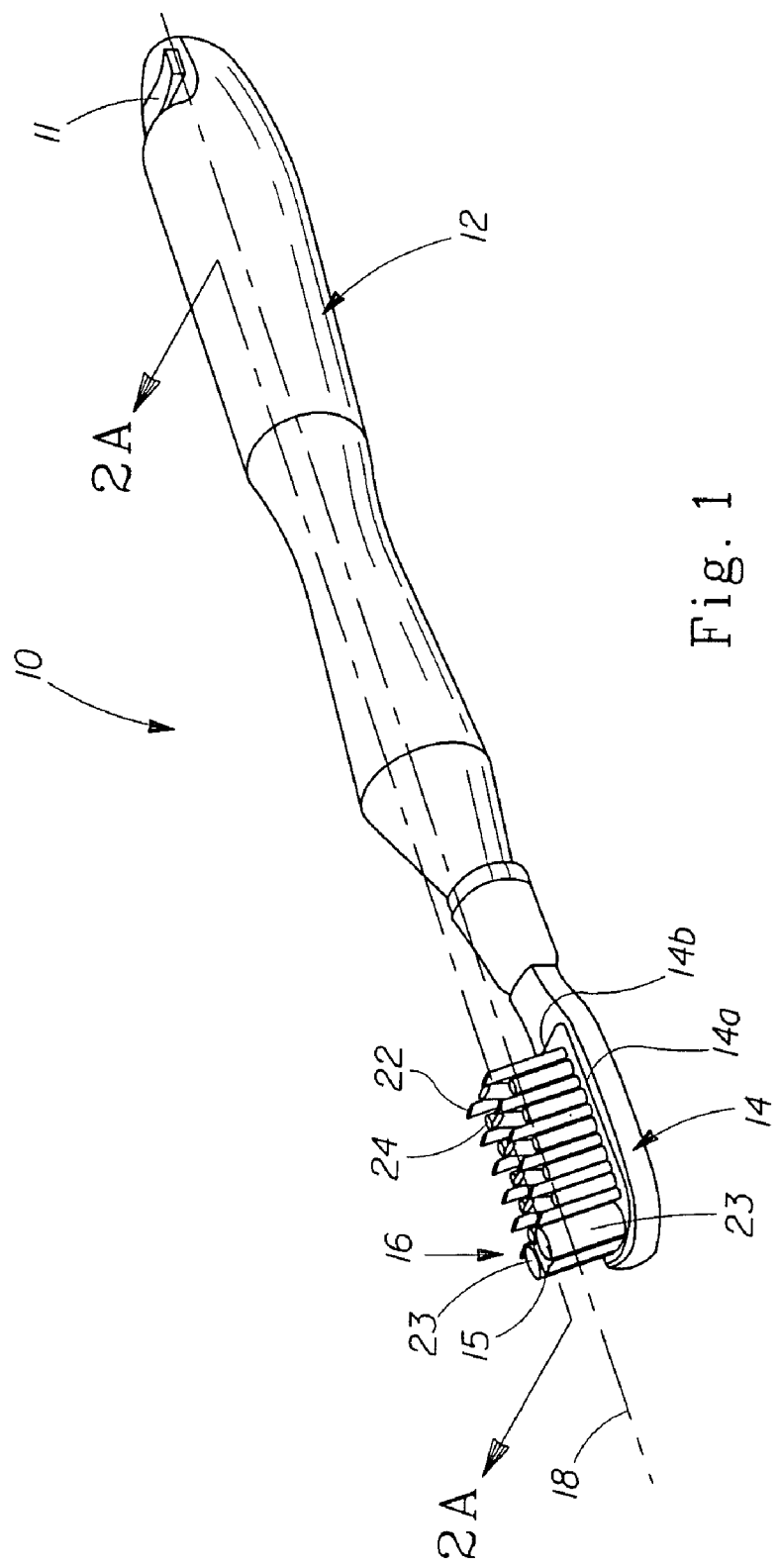
FIG. 1 is a perspective view of a toothbrush constructed according to the principles of the present disclosure.

FIG. 1 depicts an oral hygiene device constructed in accordance with the principles of the present disclosure and including, more specifically, a toothbrush 10. Generally, the toothbrush 10 includes a handle 12, a head 14, and a plurality of bristles 16. The plurality of bristles 16 is adapted for performing one or more oral cleaning operations. As is generally understood, a user holds the toothbrush 10 by the handle 12 and inserts the head 14 into his/her mouth. Through repetitive brushing motion, the user then cleans his/her teeth with the bristles 16.

For descriptive purposes, the toothbrush 10 includes a longitudinal axis 18. The head 14 may be an elongated body extending generally along the longitudinal axis 18. In some embodiments, the head 14 can be offset and/or angled with respect to the longitudinal axis 18. Additionally, embodiments are contemplated where the head 14 may be releasably connected to the handle 12 such that the head 14 may be replaced when the bristles 16 become worn.

Figure 2A:
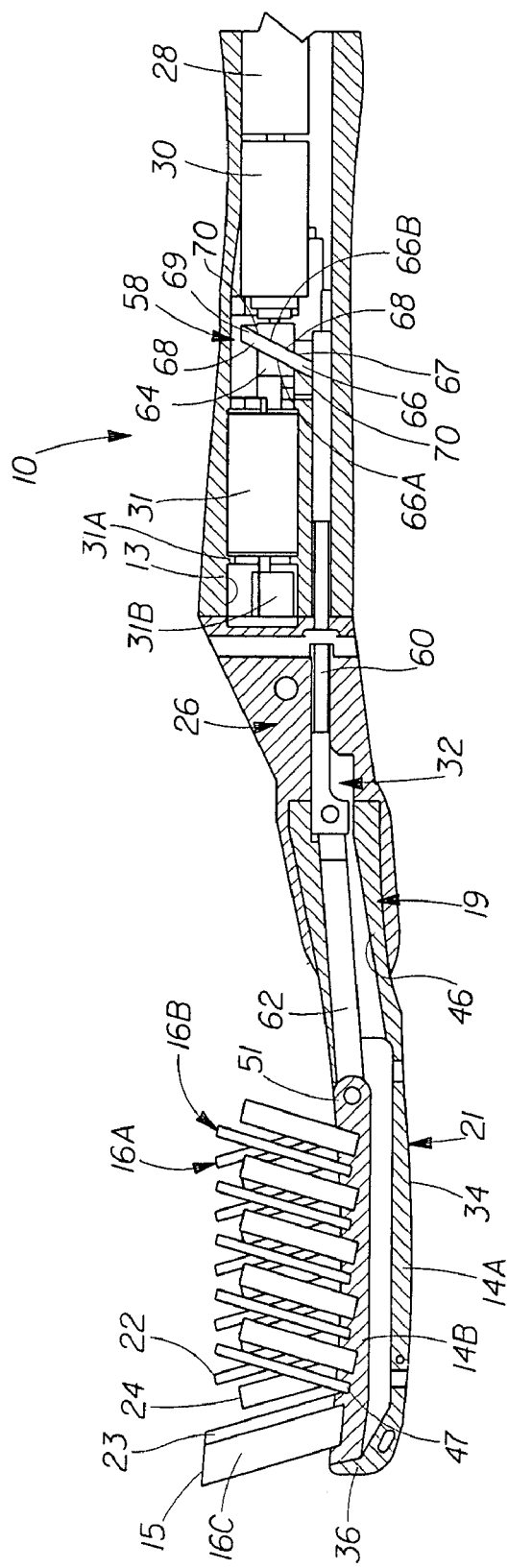
FIG. 2A is a cross-sectional side view of the toothbrush of FIG. 1, taken through line 2A-2A of FIG. 1.

As shown in FIG. 2A, the head 14 may include a fixed component 14A and a movable component 14B. As will be described hereafter, the movable component 14B can be generally disposed on the longitudinal axis 18 for sliding displacement within and relative to the fixed component 14A of the head 14, in some embodiments. In some embodiments, in order to effectuate this sliding displacement, the toothbrush 10 may further include an actuator assembly 26 controlled by a switch 11 (shown in FIG. 1). A user can manipulate the switch 11 to an "ON" position, thereby initiating the sliding displacement. Alternatively, a user can manipulate the switch 11 to an "OFF" position to terminate sliding displacement. The "ON" position may correspond to a first configuration while the "OFF" position corresponds to a second configuration or vice versa. Alternatively, manipulation of the switch 11 in rapid succession may provide an intermediate configuration for the toothbrush 10, e.g. the sliding displacement between the first configuration and the second configuration.

Additionally, embodiments are contemplated where the toothbrush 10 includes a controller circuit. Any suitable controller circuit may be utilized. In some embodiments, the controller circuit could be configured to toggle the moveable component 14B between positions when the switch is turned to the "ON" position. In some embodiments, the controller circuit could be configured to toggle the movable component 14B between positions over a given time period when the switch 11 is turned to the "ON" position and left on. The given time period for such embodiments may vary between about 1 hour to about 24 hours, in some embodiments. In some embodiments, the time period may be greater than about 1 hour, greater than about 2 hours, greater than about 3 hours, greater than about 4 hours, greater than about 5 hours, greater than about 6 hours, greater than about 7 hours, greater than about 8 hours, greater than about 9 hours, greater than about 10 hours, greater than about 11 hours, greater than about 12 hours, greater than about 13 hours, greater than about 14 hours, greater than about 15 hours, greater than about 16 hours, greater than about 17 hours, greater than about 18 hours, greater than about 19 hours, greater than about 20 hours, greater than about 21 hours, greater than about 22 hours, greater than about 23 hours and/or less than about 24 hours, less than about 23 hours, less than about 22 hours, less than about 21 hours, less than about 20 hours, less than about 19 hours, less than about 18 hours, less than about 17 hours, less than about 16 hours, less than about 15 hours, less than about 14 hours, less than about 13 hours, less than about 12 hours, less than about 11 hours, less than about 10 hours, less than about 9 hours, less than about 8 hours, less than about 7 hours, less than about 6 hours, less than about 5 hours, less than about 4 hours, less than about 3 hours, less than about 2 hours, or less than about 1 hour. One advantage of such embodiments is that the controller circuit may be configured to modify the configuration of the toothbrush automatically such that the user utilizes the proper configuration at the proper brushing time.

In one specific embodiment, the actuator assembly 26 may cycle the movable component 14B between multiple positions at a relatively low frequency. Accordingly, the actuator assembly 26 may also manipulate the entire head 14 between multiple configurations to optimize and vary the cleaning function of the toothbrush, as will be described in much greater detail below. Such changing of configurations may occur independently of any other brushing motion and may not replace a user's brushing motion.

Referring back to the head 14 of the toothbrush 10, as depicted in FIG. 2A, the bristles 16 include an outer bristle field 16A, an inner bristle field 16B, and optionally, an auxiliary bristle field 16C. The outer bristle field 16A may extend from the fixed component 14A, and the inner bristle field 16B may extend from the movable component 14B. In some embodiments, the auxiliary bristle field 16C may extend from the fixed component 14A and/or the movable component 14B.

Figure 2B:
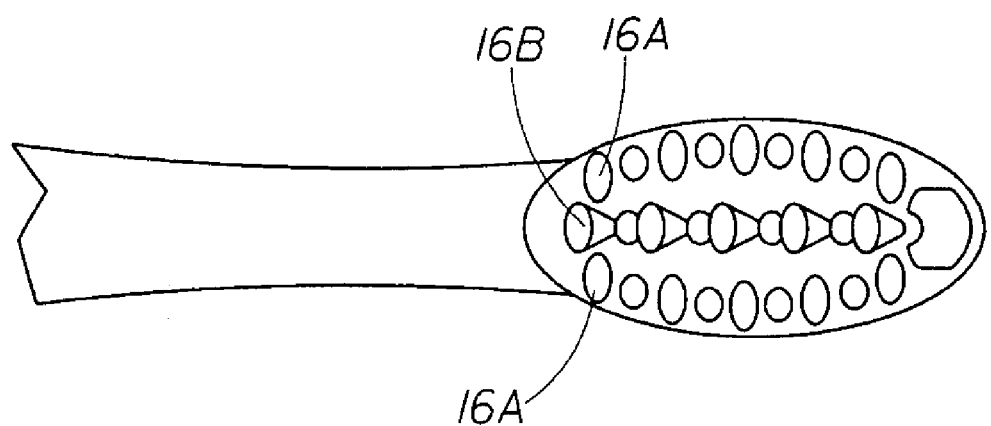
FIG. 2B is a perspective view showing a head and neck of the toothbrush of FIG. 1.

As shown in FIG. 2B, in some embodiments, the outer bristle field 16A may include two rows of bristle tufts while the inner bristle field 16B includes a single row of bristle tufts. The single row of bristle tufts in the inner bristle field 16B may be disposed parallel to and between the two rows of the outer bristle field 16A, in some embodiments.

In the embodiment shown in FIGS. 2A-2D, both the outer and inner bristle fields 16A, 16B include a plurality of nail tufts 22 and a plurality of support tufts 24. In general, the nail tufts 22 have a narrow aspect ratio (in cross section) that better allows filaments of the nail tufts 22 to penetrate between teeth compared to tuft shapes with a wider aspect ratio. The nail tufts 22 can provide interproximal and gum cleaning. The support tufts 24 of can provide surface cleaning including surface plaque removal.

Figure 2C:
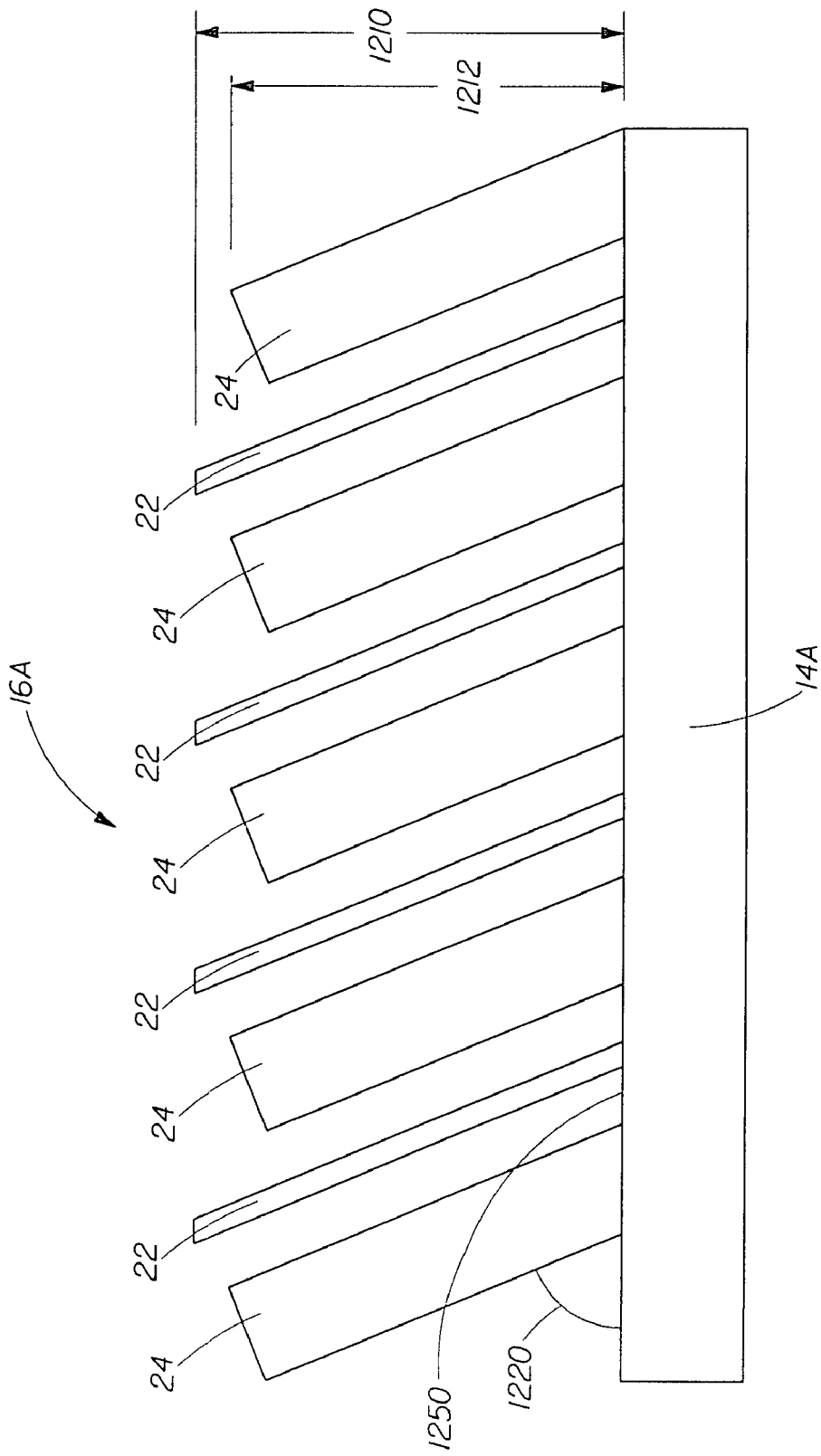
FIGS. 2C and 2D are elevation views showing tuft orientations with respect to the head of the toothbrush of FIG. 1.
Figure 2D:
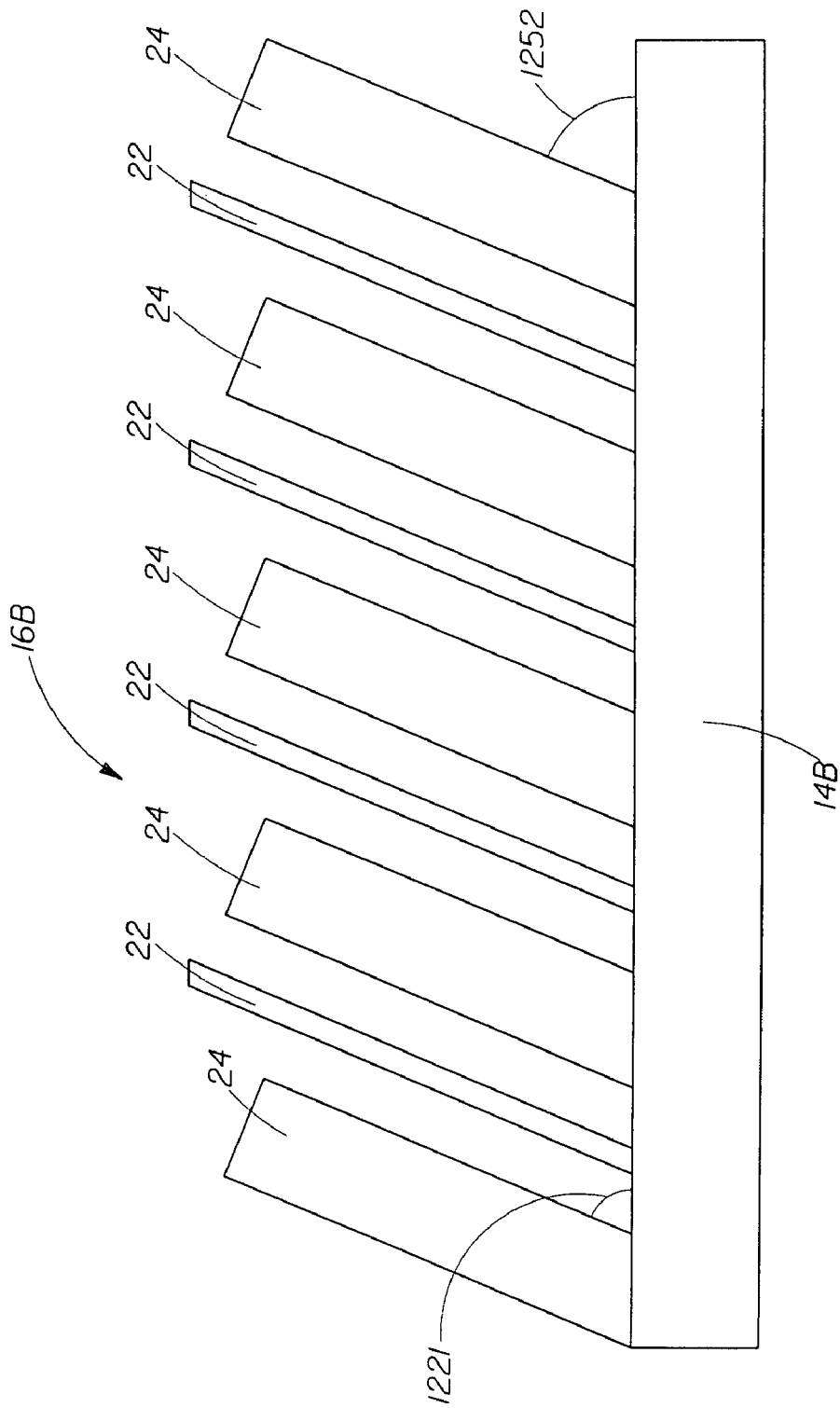

As illustrated in FIGS. 2C and 2D, in some embodiments, the nail tufts 22 and/or the support tufts 24 of the outer bristle field 16a may be disposed at an angle 1220 relative to the head 14. Embodiments are contemplated where the support tufts 24 are disposed at an angle relative to the head 14 which is greater than an angle at which the nail tufts 22 are disposed relative to the head 14. Additionally, embodiments are contemplated where the support tufts 24 are disposed at an angle relative to the head 14 which is less than an angle at which the nail tufts 22 are disposed relative to the head 14. Additional embodiments are contemplated where a portion of the support tufts 24 are disposed at an angle relative to the head 14 which is greater than that of the nail tufts 22, and a portion of the support tufts 24 are disposed at an angle relative to the head 14 which is less than that of the nail tufts 22. The support tufts 24 and/or the nail tufts 22 can be configured as described above with regard to the outer bristle field 16A and/or the inner bristle field 16B. In alternative embodiments, the nail tufts 22 and/or support tufts 24 may be mounted at compound angles, where the tufts may be additionally mounted at angles transverse to the longitudinal axis 18.

In some embodiments, the nail tufts 22 and/or support tufts 24 of the outer bristle field 16A may be disposed at an angle 1220 relative to the head 14 which is substantially equal and opposite to an angle 1221 of the nail tufts 22 and/or support tufts 24 of the inner bristle field 16B. In some embodiments, the angle 1220 and/or 1221 can be between about 60 degrees to about 160 degrees or any individual number within the range, relative to the head 14. In some embodiments, the angle 1220 and/or the angle 1221 may be greater than about 45 degrees, greater than about 50 degrees, greater than about 55 degrees, greater than about 60 degrees, greater than about 65 degrees, greater than about 70 degrees, greater than about 75 degrees, greater than about 80 degrees, greater than about 85 degrees, greater than about 90 degrees, greater than about 95 degrees, greater than about 100 degrees, greater than about 105 degrees, greater than about 110 degrees, greater than about 115 degrees, greater than about 120 degrees, greater than about 125 degrees, greater than about 130 degrees, greater than about 135 degrees, greater than about 140 degrees, greater than about 145 degrees, greater than about 150 degrees, greater than about 155 degrees, and/or less than about 160 degrees, less than about 155 degrees, less than about 150 degrees, less than about 145 degrees, less than about 140 degrees, less than about 135 degrees, less than about 130 degrees, less than about 125 degrees, less than about 120 degrees, less than about 115 degrees, less than about 110 degrees, less than about 105 degrees, less than about 100 degrees, less than about 95 degrees, less than about 90 degrees, less than about 85 degrees, less than about 80 degrees, less than about 75 degrees, less than about 70 degrees, less than about 65 degrees, less than about 60 degrees, less than about 55 degrees, or less than about 50 degrees. Other suitable angles are discussed in U.S. Pat. No. 6,308,367.

Additionally, as shown in FIGS. 2C-2D, the nail tufts 22 can be generally longer than the support tufts 24. For example, a length 1210 of the nail tufts 22 can be between about 0% to about 50% greater than a length 1212 of the support tufts 24, or any individual number within the range. As another example, the length 1210 can be between about 10% to about 29% greater than the length 1212. As yet another example, the length 1210 can be between about 21% to about 22% greater than the length 1212. Each of the lengths 1210 and 1212 is measured from a bristle facing surface 1250 of the fixed component 14A and/or a bristle facing surface 1252 of the movable component 14B.

In some embodiments, the length 1210 of the nail tufts 22 can be greater than about 0% of the length 1212 of the support tufts, greater than about 5%, greater than about 10%, greater than about 15%, greater than about 20%, greater than about 25%, greater than about 30%, greater than about 35%, greater than about 40%, greater than about 45% and/or less than about 50%, less than about 45%, less than about 40%, less than about 35%, less than about 30%, less than about 25%, less than about 20%, less than about 15%, less than about 10%, or less than about 5%.

Referring back to FIG. 2A, the auxiliary bristle field 16C may include a primary tuft 15 and a pair of secondary tufts 23. In some embodiments, the primary tuft 15 may extend from the movable component 14B of the head 14 while the secondary tufts 23 may extend beside the primary tuft 15 from the fixed component 14A of the head 14. In contrast, embodiments are contemplated where the primary tuft 15 and the secondary tufts 23 each extend from the movable component 14B or each extend from the fixed component 14B. Also, embodiments are contemplated where the bristle field 16C includes a single tuft which comprises the primary tuft 15 and the secondary tufts 23 which can extend from either the fixed component 14A or the movable component 14B.

While the auxiliary bristle field 16C is schematically depicted as including substantially solid masses, the auxiliary bristle field 16C may actually include a plurality of densely arranged bristles. The auxiliary bristle field 16C of the disclosed form therefore serves to clean areas of the oral cavity that are otherwise difficult to reach. Other suitable configurations for the auxiliary bristle field 16C as well as the bristle fields in general are described in U.S. Pat. No. 6,308,367.

While the nail tufts 22 and support tufts 24 are schematically depicted as including generally solid masses, they each may include a plurality of bristles. In alternate forms, however, the nail tufts 22 and support tufts 24, as well as the primary tuft 15 and secondary tufts 23, may be made of substantially solid elastomer bodies shaped and arranged for optimal cleaning. In embodiments where the nail tufts 22, support tufts 24, primary tuft 15, and/or the secondary tuft 23, comprise solid elastomer bodies, the solid elastomer bodies may be capable of moving relative to the head 14. For example, the solid elastomer bodies may be capable of pivoting with respect to the head 14. Suitable elastomer bodies and configurations thereof are disclosed in U.S. Pat. No. 6,553,604 filed on Mar. 16, 2000; U.S. Pat. No. 6,151,745 filed on Jul. 12, 1999; U.S. Pat. No. 5,987,688 filed on Oct. 30, 1996; U.S. Patent Application Publication Nos. 2004/0177462 filed on Mar. 14, 2003; and 2005/0235439 filed on Apr. 23, 2004.

For example, embodiments are contemplated where the outer bristle field 16A and/or the inner bristle field 16B include fins. The fins may be elastomeric. The fins may be snap fitted into the fixed component 14A and/or the movable component 14B. The fins may be adhesively attached fixed component 14A and/or the movable component 14B. The fins may be attached to fixed component 14A and/or the movable component 14B via any suitable method. Some suitable methods are disclosed in U.S. Pat. No. 6,553,604 and U.S. Patent Application Publication No. 2005/0235439.

In some embodiments, the fins may comprise ridges. The ridges may be integrally formed with the fins. Alternatively, the ridges may be formed from a second material which is different from a material utilized for the fins. In some embodiments, the ridges may be formed from the same material as the fins, e.g. thermoplastic elastomers. Suitable materials, processes, and design for the ridges and the fins are further described in U.S. Patent Application Publication No. 2005/0235439.

The configuration of the bristles 16 allows the disclosed form of the toothbrush 10 to generally and selectively provide surface cleaning, as well as interproximal and gum cleaning. Additionally, as mentioned above, an actuator assembly 26 (shown in FIG. 2A) may aid these functions by selectively moving the movable component 14B including the inner and/or auxiliary bristle fields 16B, 16C between a first position (shown in FIG. 4A) and a second position (shown in FIG. 4B). In some embodiments, depending on the position of the movable component 14B, the entire head 14 of the toothbrush 10 is adapted to embody one of at least two configurations for providing various cleaning operations, as will be discussed in detail below.

Referring again to FIG. 2A, the actuator assembly 26 can be disposed within a cavity 13 of the handle 12 of the toothbrush 10. In some embodiments, the actuator assembly 26 includes a power source 28, a first motor 30, a second motor 31, and a drivetrain 32. The power source 28 is schematically depicted to include, for example, a battery such as a AA or AAA battery. The first motor 30 may include an electric motor powered by the battery and may include an output shaft 30A (shown in FIG. 3). The second motor 31 may include an electric motor, which may also be powered by the battery, having an output shaft 31A and an eccentric weight 31B.

The drivetrain 32 may operably couple the first motor 30 to the movable component 14B of the head 14. The first motor 30 may operate as a conventional rotary motor to spin the output shaft 30A and drive the drivetrain 32. The second motor 31 may also include a conventional rotary motor; however, upon actuation, the eccentric weight 31B, which is attached to the output shaft 31A, may cause the toothbrush to vibrate similarly to the Oral-B Pulsar™ toothbrush that is commercially available from The Procter & Gamble Company and described in U.S. Pat. No. 6,564,416. Additionally, embodiments are contemplated where a user may select between actuation of either or both of the motors 30, 31. In some embodiments, the motors 30, 31 may work in conjunction with each other, and/or independently of one another.

Figure 3:
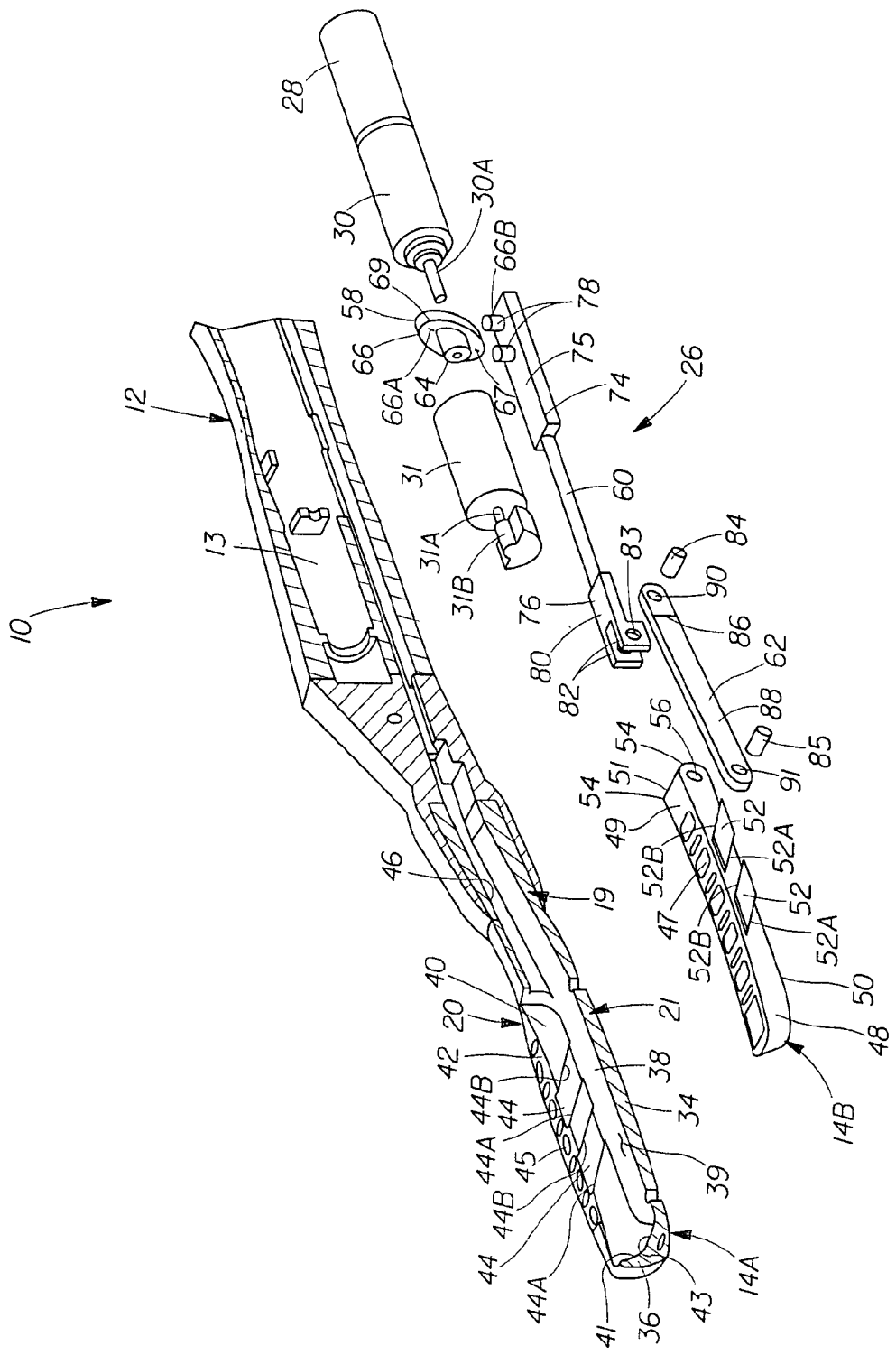
FIG. 3 is an exploded partial cross-sectional perspective view of the toothbrush of FIGS. 1 and 2 with bristles removed.

With continued reference to FIG. 2A, as well as FIG. 3, the handle 12, the fixed component 14A, and the movable component 14B may be separate components. These components may be formed separately and subsequently assembled. As mentioned above, the handle 12 may include a cavity 13 containing the actuator assembly 26. In the depicted form of the handle 12, the cavity 13 is complexly shaped to securely accommodate each of the components of the actuator assembly 26, as well as a portion of the fixed component 14A of the head 14. However, in an alternate form, the cavity 13 may be uniformly shaped and the components of the actuator assembly 26 may be fixed therein with an adhesive or some other device. In still another form, the fixed component 14A of the head 14 and handle 12 may be formed of a single piece. In yet another form, the head 14 and/or neck portion 19 of the brush can be replaced. For example, the after a period of use, a consumer may be able to separately purchase a replacement head and/or neck portion and utilize the original handle 12 of the brush 10 with the replacement head and/or neck portion.

With specific reference to FIG. 3, the fixed component 14A may include an elongated body defining the periphery of the head 14. More specifically, the fixed component 14A includes the neck portion 19 and a body portion 21. The body portion 21 includes a base 34, a pair of sides 20 (one of which is shown in FIG. 3), and a toe 36. The pair of sides 20 and the toe 36 extend generally upward from the base 34 relative to the orientation of FIGS. 2 and 3. The base 34 and toe 36 extend between and connect the sides 20. Each of the sides 20 includes an inner sidewall 40 and a top surface 42. In some embodiments, each inner sidewall 40 may define a pair of slots 44. In some embodiments, the top surfaces 42 may define a plurality of angled bores 45 capable of fixedly receiving the outer bristle field 16A. In combination, the inner sidewalls 40 of the sides 20, the base 34, and toe 36 may define an elongated recess 38 in the fixed component 14A. The recess 38 contains the movable component 14B. An intermediate surface 43 may extend at an incline from the top surface 39 of the base 34 to the inner surface 41 of the toe 36.

The slots 44 can be generally shaped for guiding the movable component 14b between the first and second positions, as will be described in more detail below. Each of the slots 44 includes a forward surface 44A and a rearward surface 44B.

The neck 19 of the fixed component 14A may define a through-bore 46, in some embodiments. The through-bore 46 extends generally along the longitudinal axis 18 of the toothbrush and may communicate with the recess 38 and the cavity 13 in the handle 12. The through-bore 46 accommodates a portion of the drivetrain 32 of the actuator assembly 26.

The movable component 14B can be a generally elongated body having a pair of opposing sidewalls 48, a top surface 49, a bottom surface 50, and a connector 51. In some embodiments, the opposing sidewalls 48 may each define a pair of bosses 52. The bosses 52 can be generally shaped to fit in the slots 44 in the inner sidewalls 40 of the fixed component 14A. Similar to the slots 44 in the fixed component 14A, the bosses 52 each include a forward surface 52A and a rearward surface 52B. A dimension of the forward and rearward surfaces 52A, 52B of the bosses 52 is less than a dimension of the forward and rearward surfaces 44A, 44B of the slots 44. This enables the bosses 52 to be disposed within the slots 44 for sliding displacement parallel to the surfaces 44A, 44B, 52A, 52B. The forward and rearward surfaces 52A, 52B of the bosses 52 therefore slidably engage the forward and rearward surfaces 44A, 44B of the slots 44, respectively. So configured, the angle of the slots 44 and bosses 52 define the path along which the movable component 14B travels between the first and second positions. Further, similar to the top surface 42 of the fixed component 14A, in some embodiments, the top surface 49 of the movable component 14B includes a plurality of angled bores 47 fixedly receiving the inner bristle field 16B. Finally, the connector 51 of the movable component 14B may include, in some embodiments, a pair of tabs 54 defining apertures 56. The apertures 56 can connect to the drivetrain 32 of the actuator assembly 26. In an alternative embodiment, which will be described in detail below with reference to FIG. 8, the drivetrain 32 and the movable component 14B of the head 14 may be constructed as a one-piece integral member.

Referring still to FIGS. 2A and 3 and as mentioned above, the actuator assembly 26 may include the power source 28, the first and second motors 30, 31, and the drivetrain 32. The drivetrain 32 may include a drive cam 58, a linear follower link 60, and an articulation link 62. The drive cam 58 includes a central portion 64 and a flange 66.

The central portion 64 can be generally cylindrical and can be attached to the output shaft 30A of the first motor 30. The flange 66 may extend radially from the central portion 64 at an angle less than about ninety-degrees. In some embodiments, the flange 66 may be connected to the output shaft 30A and extend radially outward therefrom. The flange 66 includes an axially forward portion 67 and an axially rearward portion 69. In one form, the flange 66 is disposed at an angle of approximately 60° relative to the central portion 64 of the drive cam 58.

The flange 66 may be disposed at any suitable angle with respect to the central portion 64. For example, the flange 66 may be disposed at an angle which is less than about 90 degrees and greater than about 5 degrees. In some embodiments, the flange 66 may be disposed at an angle which is greater than about 5 degrees, greater than about 10 degrees, greater than about 15 degrees, greater than about 20 degrees, greater than about 25 degrees, greater than about 30 degrees, greater than about 35 degrees, greater than about 40 degrees, greater than about 45 degrees, greater than about 50 degrees, greater than about 55 degrees, greater than about 60 degrees, greater than about 65 degrees, greater than about 70 degrees, greater than about 75 degrees, greater than about 80 degrees, greater than about 85 degrees, and/or less than about 90 degrees, less than about 85 degrees, less than about 80 degrees, less than about 75 degrees, less than about 70 degrees, less than about 65 degrees, less than about 60 degrees, less than about 55 degrees, less than about 50 degrees, less than about 45 degrees, less than about 40 degrees, less than about 35 degrees, less than about 30 degrees, less than about 25 degrees, less than about 20 degrees, less than about 15 degrees, or less than about 10 degrees.

The flange 66 further defines a first surface 66a and a second surface 66B connecting the axially forward and rearward portions 67, 69. The second surface 66B is disposed opposite the flange 66 from the first surface 66A. The second surface 66B is disposed generally parallel to the first surface 66A. When viewed from an axial direction, the flange 66 includes a cylindrical ring disposed concentrically around the central portion 64. When viewed from the side, as depicted in the FIG. 2A, for example, the flange 66 is angled relative to the central portion 64. The angled orientation of the flange 66 is defined by the orientation of the first and second surfaces 66A, 66B.

Referring back to FIG. 2A, the first and second surfaces 66A, 66B are generally angled, as mentioned, but may have complex geometries, in some embodiments. Specifically, each of the first and second surfaces 66A, 66B may include a concave portion 68 and a convex portion 70. The concave and convex portions 68, 70 may smoothly transition along a circumferential path on the inclined surfaces 66A, 66B. In operation, the concave and convex portions 68, 70 serve to smoothly displace the linear follower link 60, as will be described in more detail below. In some embodiments, the first and second surfaces 66A, 66B may be substantially planar surfaces.

As shown in FIG. 3, in some embodiments, the linear follower link 60 may include a generally long straight body having a first end 74 and a second end 76. The first end 74 may include a plate 75 supporting a pair of bosses 78. The bosses 78 may extend upward from the plate 75 and may be spaced apart such that the bosses 78 may receive the flange 66 therebetween, as depicted in FIGS. 2A, 4A and 4B. The second end 76 of the linear follower link 60 includes a connector 80. In some embodiments, the connector 80 may include a pair of opposing plate portions 82 having apertures 83. A pin 84 may extend through the apertures 83 and operatively connect the linear follower link 60 to the articulation link 62.

The articulation link 62, similar to the linear follower link 60, in some embodiments, may include a generally long straight body having a first end 86 and a second end 88. The first end 86 may include an aperture 90. The aperture 90 may receive the pin 84 to connect to the connector 80 of the second end 76 of the linear follower link 60. So configured, the articulation link 62 may pivot about the pin 84. The second end 88 of the articulation link 62 may also include an aperture 91. As depicted in FIGS. 2A, 4A and 4B, the aperture 91 may receive a pin 85, which is also received in the apertures 56 in the connector 51 of the movable component 14B. So configured, the articulation link 62 may also pivot about the pin 85 relative to the movable component 14B of the head 14. While the drivetrain 32 has just been described as including separate linear follower and articulation links 60, 62 the drivetrain 32 may include a single integral piece, as mentioned above and depicted in FIG. 8, which will be described in more detail below.

In some embodiments, the drivetrain 32 may further comprise at least one gear or other means which can be utilized to reduce the rotational speed of the output shaft and to gain mechanical advantage. For example, a planetary gearset can be utilized to accomplish the reduced rotational speed of the output shaft 30A and to accomplish a mechanical advantage. The gear may be disposed within the motor housing or exterior thereto.

During operation, the power source 28, for example a battery, may provide electrical energy to the first motor 30. The output shaft 30A of the first motor 30 may then effect a rotation of the drive cam 58. As the drive cam 58 rotates, the flange 66 rotates and the inclined surfaces 66A, 66B continuously slidably engage the bosses 78 on the linear follower link 60. This sliding engagement converts the rotational motion of the first motor 30 into linear displacement of the linear follower link 60. The linear follower link 60 thus drives the articulation link 62 and finally, the movable component 14B.

For example, FIG. 4A illustrates the movable component 14B in the first position, which defines a first configuration for the entire head 14 of the toothbrush 10. In this position, the axially forward portion 67 of the flange 66 of the drive cam 58 engages the bosses 78 on the linear follower link 60. So configured, the linear follower link 60 is disposed in its leftmost position relative to the orientation of FIGS. 4A and 4B. Consequently, the articulation link 62 is disposed in its leftmost position. Additionally, the movable component 14B of the head 14 is disposed in its left-most and upward-most position relative to the fixed component 14A. So positioned, the outer bristle field 16A and the inner bristle field 16B are generally aligned in height. Said another way, the outer bristle field 16A terminates at a first plane, which is identified by reference numeral 92 in FIGS. 4A and 4B, while the inner bristle field 16B terminates at a second plane, which is identified by reference numeral 94 in FIG. 4A. In the first configuration, the first and second planes 92, 94 are generally the same plane. Thus, FIG. 4A depicts the bristles 16 of the toothbrush 10 including the outer bristle field 16A and the inner bristle field 16B defining a first configuration of the head 14.

In this first configuration, the outer bristle field 16A is adapted to perform a first cleaning operation, while the inner bristle field 16B is adapted to perform a second cleaning operation. The first and second cleaning operations are generally identical, but direction dependent. The first and second cleaning operations each include a surface cleaning operation, as well as an interproximal cleaning operation. Additionally, a force applied to the head 14 of the toothbrush 10 during cleaning with the first configuration of the head 14, is substantially uniformly distributed across the outer and inner bristle fields 16A, 16B.

For example, during brushing, when the head 14 is moved in the forward direction, which is to the left relative to the orientation of FIGS. 4A and 4B, the outer bristle field 16A can be angled into the direction of travel and performs the first cleaning operation. The first cleaning operation includes the support tufts 24 of the outer bristle field 16A primarily providing surface cleaning and the nail tufts 22 primarily providing interproximal cleaning. Simultaneously, the inner bristle field 16B may provide some degree of cleaning, but not as aggressively as the outer bristle field 16A because the inner bristle field 16B is angled away from the direction of travel. Alternatively, when the head 14 is moved in the rearward direction, which is to the right relative to the orientation of FIGS. 4A and 4B, the inner bristle field 16B is angled into the direction of travel and performs the second cleaning operation. The second cleaning operation includes the support tufts 24 of the inner bristle field 16B primarily providing surface cleaning and the nail tufts 22 primarily providing interproximal cleaning. Simultaneously, the outer bristle field 16A may provide some degree of cleaning, but not as aggressively as the inner bristle field 16B because the outer bristle field 16A is angled away from the direction of travel.

As the first motor 30 rotates the drive cam 58 to the second position indicated in FIG. 4B, which defines a second configuration for the entire head 14 of the toothbrush 10, the axially rearward portion 69 of the flange 66 becomes disposed between the bosses 78 on the linear follower link 60. So configured, the linear follower link 60 is disposed in its right-most position, relative to the orientation of FIGS. 4A and 4B. Consequently, the articulation link 62 is disposed in its right-most position. Finally, the movable component 14B of the head 14 is disposed in its right-most and downward-most position relative to the fixed component 14A. In this second position, the outer bristle field 16A extends a predetermined distance beyond the inner bristle field 16B. Said another way, while the outer bristle field 16A still terminates at the first plane 92, the inner bristle field 16B terminates at a third plane, which is identified by reference numeral 96 in FIG. 4B. The third plane 96 is generally parallel to and offset below the first plane 92. The third plane 96 is also parallel to and offset below the second plane 94. In one form, the third plane 96 is disposed approximately between about 0 to about 10 millimeters below the second plane 94 or any individual number within the range. Thus, FIG. 4B depicts the bristles 16 of the toothbrush 10 including the outer bristle field 16a and the inner bristle field 16b defining a second configuration of the head 14.

In some embodiments, the third plane 96 may be disposed a distance which is greater than about 0 mm below the first plane 92 and/or the second plane 94. In some embodiments, the third plane 96 may be disposed a distances greater than about 1 mm, greater than about 2 mm, greater than about 3 mm, greater than about 4 mm, greater than about 5 mm, greater than about 6 mm, greater than about 7 mm, greater than about 8 mm, greater than about 9 mm, and/or less than about 10 mm, less than about 9 mm, less than about 8 mm, less than about 7 mm, less than about 6 mm, less than about 5 mm, less than about 4 mm, less than about 3 mm, less than about 2 mm, or less than about 1 mm.

In this second configuration, the inner bristle field 16B is adapted to perform a third cleaning operation and the outer bristle field 16A is adapted to perform a fourth cleaning operation. The third cleaning operation performed by the inner bristle field 16B provides both a surface cleaning operation and an interproximal cleaning operation that is generally identical to the first and second cleaning operations described above. Additionally, as will be described further below, the third cleaning operation includes the inner bristle field 16B performing a supportive function.

More specifically, the varying heights of the outer and inner bristle fields 16A, 16B in the second configuration causes the inner bristle field 16B to engage the surface of the teeth while the outer bristle field 16A penetrates deeply into the interproximal cavities. So configured, the outer bristle field 16A bears the majority of a force applied to the head 14, which allows the outer bristle field 16A to more deeply engage the interproximal cavities. Such deeper interproximal penetration by the outer bristle field 16A defines the fourth cleaning operation. The fourth cleaning operation performed by the outer bristle field 16A is therefore enhanced because the majority of the force applied to the head 14 of the toothbrush 10 is borne by the outer bristle field 16A. Thus, in the form described herein, the effectiveness of the fourth cleaning operation performed by the outer bristle field 16a is dependent on the third cleaning operation performed by the inner bristle field 16B.

Therefore, it should be appreciated that as the first motor 30 rotates the drive cam 58, the drive cam 58 displaces the linear follower link 60, which in turn displaces the articulation link 62 and the movable component 14B, in some embodiments. More specifically, as the drive cam 58 displaces the linear follower link 60 from the first position illustrated in FIG. 4A to the second position illustrated in FIG. 4B, for example, the linear follower link 60 pulls the articulation link 62 and causes it to slightly rotate in the counterclockwise direction. Additionally, in some embodiments, as the articulation link 62 pulls the movable component 14B from the first position illustrated in FIG. 4A to the second position illustrated in FIG. 4B, the rearward surfaces 52B of the bosses 52 on the movable component 14B slidably displace along the rearward surfaces 44B of the slots 44 in the fixed component 14A. Accordingly, the opposite occurs when the drive cam 58 displaces the movable component 14B from the second position illustrated in FIG. 4B to the first position illustrated in FIG. 4A. Specifically, as the drive cam 58 displaces the linear follower link 60 from the second position illustrated in FIG. 4B to the first position illustrated in FIG. 4A, the linear follower link 60 may push the articulation link 62 and cause it to slightly rotate in the clockwise direction. Additionally, as the articulation link 62 pushes the movable component 14B between the second position illustrated in FIG. 4B to the first position illustrated in FIG. 4A, the forward surfaces 52A of the bosses 52 on the movable component 14B may slidably displace along the forward surfaces 44a of the slots 44 in the fixed component 14a. Thus, during use, the actuator assembly 26 may displace the inner bristle field 16B between two heights and longitudinal positions relative to the outer bristle field 16A thereby defining the two configurations of the head 14 discussed above.

Alternatively, the movable component 14B and/or the fixed component 14A may be configured such that when the axially forward portion 67 of the flange 66 of the drive cam 58 engages the bosses 78, the brush can be in the second configuration as described above. Correspondingly, when the axially rearward portion 69 of the flange 66 of the drive cam 58 engages the bosses 78, the brush can be in the first configuration as described above. These embodiments may be accomplished via any suitable means. For example, the angle of the slots in the fixed component 14A and/or the movable component 14B may be modified in accordance with such embodiments.

The bristle contact surface area in a given plane may vary greatly from the first configuration to the second configuration. The total bristle contact surface area is the sum of the bristle contact surface areas in the first plane 92 and the second plane 94 and is 100% in the first configuration. In some embodiments, the second configuration may reduce the total bristle contact surface area by between about 5% to about 80%, or any individual number within the range. In some embodiments, the second configuration may reduce the total bristle contact surface area by greater than about 5%, greater than about 10% greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75%, and/or less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, or less than about 5%.

In some embodiments, as shown in FIG. 5A, when the axially forward portion 67 of the flange 66 of the drive cam 58 engages the bosses 78 on the linear follower link 60, the brush can be in a second configuration. As shown, in some embodiments, when the movable component 14B of the head 14 is disposed in its left-most and upward-most position relative to the fixed component 14A, the inner bristle field 16B can terminate in a fourth plane 196 and the outer bristle field 16A can terminate in the first plane 92. As shown in FIG. 5A, the first plane 92 can be generally parallel and offset below the fourth plane 196. The distance between the fourth plane 196 and the first plane 92 can be as described above with regard to the distance between the third plane 96 and the first plane 92 and/or the second plane 94.

With regard to the second configuration shown in FIG. 5A, the outer bristle field 16A is adapted to perform a third cleaning operation and the inner bristle field 16b is adapted to perform a fourth cleaning operation. The third cleaning operation performed by the outer bristle field 16A may provide both a surface cleaning operation and an interproximal cleaning operation that is generally identical to the first and second cleaning operations described above. Additionally, as will be described further below, the third cleaning operation includes the outer bristle field 16A performing a supportive function.

More specifically, the varying heights of the outer and inner bristle fields 16A, 16B in the second configuration causes the outer bristle field 16A to engage the surface of the teeth while the inner bristle field 16B penetrates deeply into the interproximal cavities. So configured, the inner bristle field 16B bears the majority of a force applied to the head 14, which allows the inner bristle field 16B to more deeply engage the interproximal cavities. Such deeper interproximal penetration by the inner bristle field 16B defines the fourth cleaning operation. The fourth cleaning operation performned by the inner bristle field 16B is therefore enhanced because the majority of the force applied to the head 14 of the toothbrush 10 is borne by the inner bristle field 16B.

As shown in FIG. 5B, in some embodiments, when the axially rearward portion 69 of the flange 66 of the drive cam 58 engages the bosses 78 on the linear follower link 60, the brush can be in the first configuration as described above. As shown, in some embodiments, when the movable component 14B of the head 14 is disposed in its right-most and downward-most position relative to the fixed component 14A, the inner bristle field 16B can terminate in the second plane 94 and the outer bristle field 16A can terminate in the first plane 92. As shown in FIG. 5B, in the first configuration, the first and second planes 92, 94 are generally the same plane.

As discussed previously, the total bristle contact surface area is the sum of the bristle contact surface areas in the first plane 92 and the second plane 94 and is 100% in the first configuration. As such, the second configuration, shown in FIG. 5A, may impact the total bristle contact surface area as described above except with regard to the bristle contact area in the fourth plane 196.

In some embodiments, the actuator assembly 26 may cycle the movable component 14B between the first and second positions no more frequently than about every 0.5 seconds. In alternate forms, the actuator assembly 26 may displace the movable component 14B between about every 0.5 and about every 3 seconds, or any individual number within the range. This is a relatively slow frequency when compared to conventional vibrating or rotating toothbrushes. In one form of the toothbrush 10, such a slow frequency may be obtained by the particular design of the drive cam 58; the motor 30 may include a step motor; the power source 28 may include a pulsed power source; the drivetrain 32 may include a gear system; as mentioned above, a user may selectively turn the toothbrush 10 on and off via the switch 11; or combinations of the above listed means of obtaining a slow frequency. Any suitable means of achieving such a slow frequency may be utilized. Thus, it should be appreciated that the present disclosure provides a toothbrush 10 having a head 14 adapted to occupy at least two configurations in either a static or dynamic manner.

The relative displacement between the various fields of bristles 16 provides at least the following advantages. First, when the movable component 14B is disposed in the first position illustrated in FIGS. 4A and 5B, thereby defining the first configuration for the head 14, there may be no height differential between the outer and inner bristle fields 16A, 16B. This aims to effectuate both a surface cleaning operation and an interproximal cleaning operation of the toothbrush 10. Alternatively, when the movable component 14B is in the second position illustrated in FIGS. 4B and 5A, thereby defining the second configuration of the head 14, a height differential exists between the outer and inner bristle fields 16A, 16B. This places a majority of the supporting function on either the outer bristle field 16A (shown in FIG. 4B) or the inner bristle field 16B (shown in FIG. 5A), thereby enhancing the ability of the corresponding bristle field to access interproximal areas including the gums for removing plaque and other debris to prevent gingivitis and other diseases. Thus, it should be appreciated that the head 14 of the toothbrush 10 disclosed herein is capable of occupying multiple relatively static configurations, each configuration aimed at optimizing different cleaning operations. While the toothbrush 10 has been disclosed as being capable of occupying two configurations, alternate forms of the toothbrush 10 may be capable of occupying any number of configurations adapted to optimizing any number of cleaning operations.

The powered actuator assembly 26 may provide a generally smooth transition between the various configurations, but does not replace an individual user's manual brushing technique. In fact, such transition between the various configurations may be selectively intermittent. For example, one user may desirably utilize the actuator assembly 26 to merely change the head 14 from one of the first and second configurations to the other for an entire morning or evening brushing operation. In such practice, a user may simply turn the motor 30 on and quickly turn the motor 30 off, thereby stalling the movable component 14b in the desired location.

Heretofore the variance between the first configuration and the second configuration of the brush 10 has been discussed in the context of modifying the location of the movable component 14B or modifying the height of the inner bristle field 16B. However, embodiments are contemplated where the height of the outer bristle field 16A can be modified while the height of the inner bristle field 16B remains constant between the first configuration and the second configuration. For example, the brush 10 may comprise at least one movable component which includes a portion of the outer bristle field 16A while the fixed component 14A comprises a portion of the inner bristle field 16B.

While the present disclosure has, thus far, included a toothbrush 10 having a powered actuator assembly 26, it should be appreciated that an alternate form of the toothbrush may include a manual actuator assembly. For example, FIG. 6 depicts one alternate toothbrush 100 constructed according to the principles of the present disclosure having a manual actuator assembly 126. The toothbrush 100 depicted in FIG. 6 is substantially similar to the toothbrush 10 described above in that it includes a handle 112 and a head 14. In some embodiments, the handle 112 defines a cavity 113 including an elongated bore portion 113A and a pair of dimples 113B. The cavity 113 is adapted to contain the manual actuator assembly 126.

In some embodiments, the manual actuator assembly 126 includes a finger wheel 128, a shaft 130, a drive cam 58, a linear follower link 60, and an articulation link 62. The drive cam 58, linear follower link 60, and articulation link 62 may be similar to those described above and therefore a detailed description will not be repeated.

The shaft 130 has a first end 132, a second end 134. The first end 132 of the shaft 130 may be fixed to the drive cam 58. The second end 134 of the shaft 130 may be fixed to the finger wheel 128, which can be disposed outside of the cavity 113 of the handle 112.

The shaft 130 may further comprise an element which inhibits the involuntary rotation of the shaft 130. For example, as shown in FIG. 6, the shaft 130 may further comprise a detent 136. In the form depicted, the detent 136 includes a spring-loaded element and is disposed along the shaft 130 at a position generally longitudinally aligned with the dimples 113B in the cavity 113. During operation, a user may rotate the finger wheel 128 to displace the movable component 14B between the first and second positions as described above. When the movable component 14B is in the first position, the detent 136 can be disposed in one of the pair of dimples 113B. When the movable component 14B is in the second position, the detent 136 is disposed in the other of the pair of dimples 113B. Thus, the interaction between the detent 136 and the dimples 113B retain the shaft 130, and therefore, the movable component 14B in the desired position. A user may rotate the finger wheel 128 in either a clockwise or a counterclockwise direction to displace the movable component 14B as desired.

While the shaft 130 has just been described as including a detent 136 cooperating with a pair of dimples 113B in the cavity 113, any suitable means for inhibiting or precluding involuntary rotation of the shaft 130 can be implemented with the toothbrush 100. For example, an alternate form of the toothbrush 100 may include a plurality of detents disposed on the shaft 130 adapted to cooperate with a plurality of dimples 113B. In another form, the toothbrush 100 may not include conventional detents at all, but rather, a plastic snap-clip having a protrusion aligned with the dimples 113B and a lever that extends out of the cavity 113 toward the finger wheel 128 such that a user may depress the lever to release the protrusion from the dimples 113B and adjust the position of the movable component 14B. In another form, the shaft 130 may include recesses and the handle 112 may include a detent or a snap-clip. In yet another alternate form, the shaft 130 may not include detents or a protrusion at all, but rather, it may merely be frictionally fit within the cavity 113 to prevent the shaft 130 from involuntary rotation. In still another form, the toothbrush 100 may additionally include a lock or clasp mounted to the exterior of the handle 112, for example, and that is selectively operable to prevent the shaft 130 from involuntary rotation.

Additionally, while each of the forms of the present disclosure have, thus far, been described as including rotary drive actuators, an alternate form of the toothbrush 10 and/or 100 may include a linear-drive actuator. For example, FIG. 7 depicts an alternate toothbrush 200 including a linear-drive actuator assembly 226. The toothbrush 200 depicted in FIG. 7 is substantially similar to the toothbrushes 10, 100 described above in that it includes a handle 212 and a head 14 comprising a fixed component 14A and a movable component 14B. The handle 212 includes a cavity 213 containing the linear-drive actuator assembly 226.

The linear-drive actuator assembly 226 includes a manual linear-drive actuator assembly 226. Specifically, the actuator assembly 226 includes a thumb tab 228, a linear follower link 60, and an articulation link 62. The linear follower link 60 and articulation link 62 are similar to those described above with respect to FIGS. 2A-6, and therefore a detailed description will not be repeated. The thumb tab 228 is fixed to the linear follower link 60 via an appendage 230. The handle 212 defines a slot 232 receiving the appendage 230 such that the thumb tab 228 is exposed on the outside of the handle 212.

During operation, a user needs only to apply a linear force to the thumb tab 228 to thereby displace the movable component 14b between first and second positions in a manner similar to that described above. In some embodiments, the manual actuator assembly 226 may include a push-button mounted to the side of the handle 212 and operable similar to a mechanical pencil. For example, a user may actuate the push-button actuator by applying a force in the radial direction of the toothbrush 200. Upon actuation, the push-button may engage a wedge or plurality of wedges disposed within the cavity 213 to thereby transfer the radial force into a longitudinal force to move the linear follower link 60, articulation link 62, and movable component 14b of the head 14. So configured, a user may select the desired configuration of the head 14 of the toothbrush 200 with a single hand similar to the embodiment depicted in FIG. 7.

While the linear-drive actuator assembly 226 has been disclosed as being manually operated, another alternate form of the disclosure may include a powered linear-drive assembly. Such powered linear-drive actuator assembly may include a reciprocating pneumatic cylinder actuator or any other device operable to serve the principles of the present disclosure.

Figure 8A:
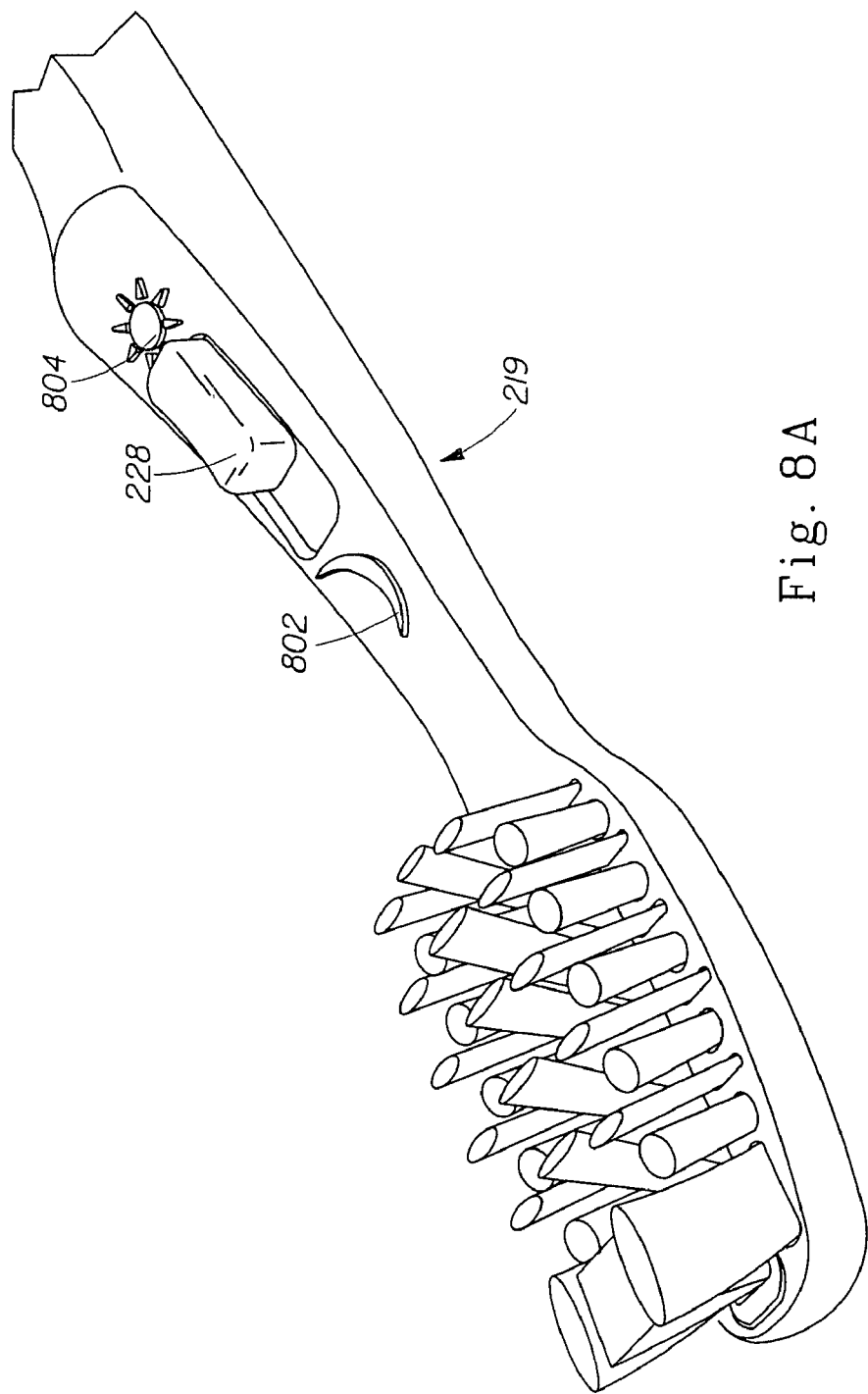
FIGS. 8A and 8B are perspective views showing a portion of a toothbrush constructed in accordance with the present invention.
Figure 8B:
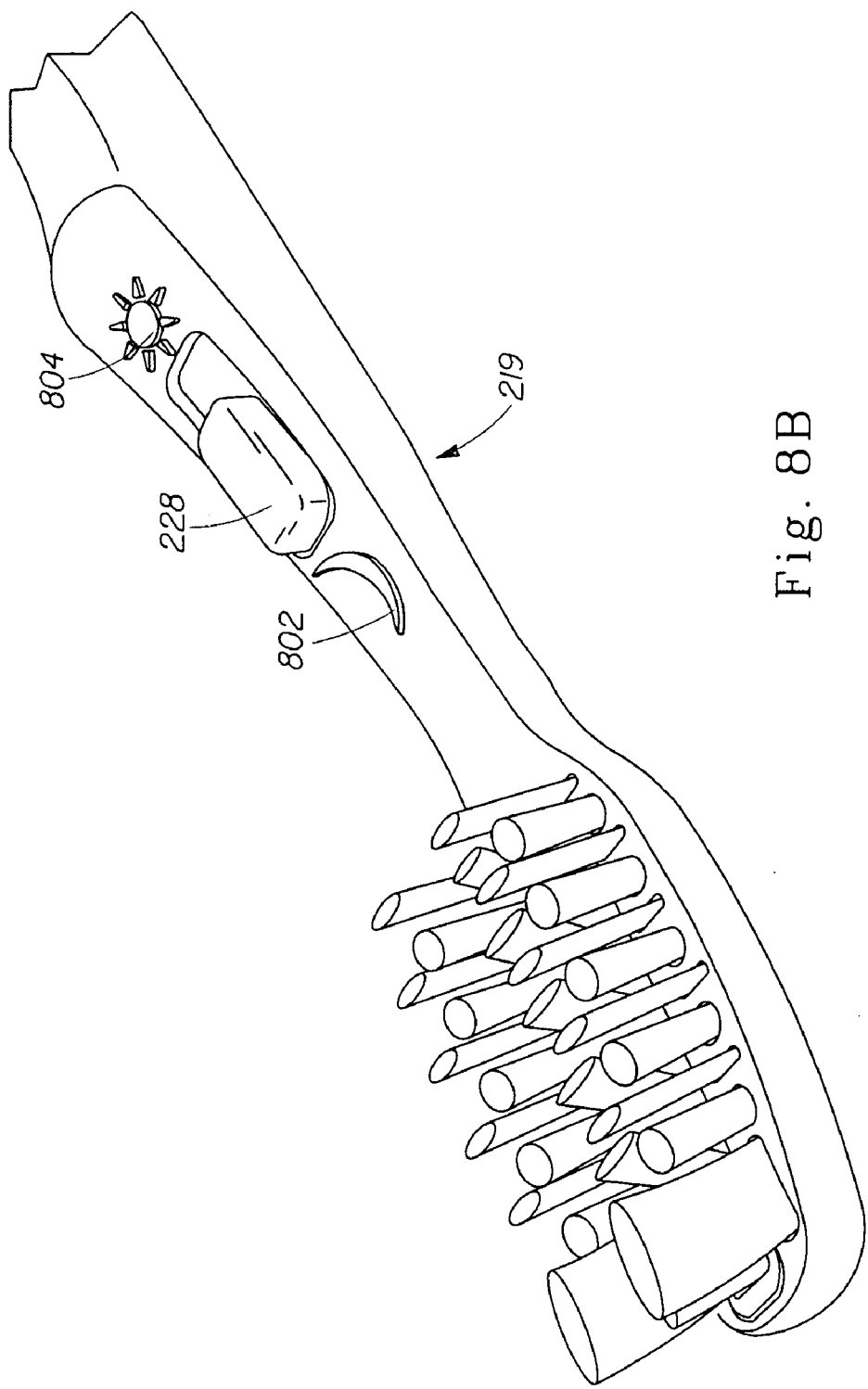

As shown, the thumb tab 228 is disposed on the handle 212 near the neck 219 of the toothbrush 200. The thumb tab 228 may be disposed in any suitable location on the toothbrush 200. For example, as shown in FIGS. 8A and 8B, the thumb tab 228 is disposed in the neck 219 of the toothbrush 200. Additionally, in some embodiments, icons 802 and/or 804 may be disposed adjacent the thumb tab 228. The icons 802 and/or 804 may communicate to the user the current configuration of the bristle fields. For example, the icons 802 and/or 804 may include alphanumeric characters which communicate either a first configuration and/or a second configuration. In some embodiments, the icons 802 and/or 804 may include graphics or symbols which communicate to the consumer the proper configuration for the time of the day.

For example, as shown in FIGS. 8A and 8B, the icons 802 and/or 804 may comprise a graphic or symbol which include a moon and a sun, respectively. The icon 802 of the moon may communicate to the consumer that the correct brushing configuration for nighttime is when the thumb tab 228 is in its upwardmost position toward the moon. Conversely, the icon 804 of the sun may communicate to the consumer that the correct brushing configuration for the daytime is when the thumb tab 228 is in its downwardmost position toward the sun.

As shown in FIGS. 8A and 8B, the icon 804 of the sun may correspond to the first configuration as described heretofore while the icon 802 of the moon may correspond to the second configuration as described heretofore. In some embodiments, the icons 802 and/or 804 may comprise any suitable combination of alphanumerical characters and graphics/symbols. Although not shown, icons, as described above may be associated with the toothbrush so as to communicate to the consumer the current configuration of the brush and/or the proper configuration for a brushing period.

Figure 9:
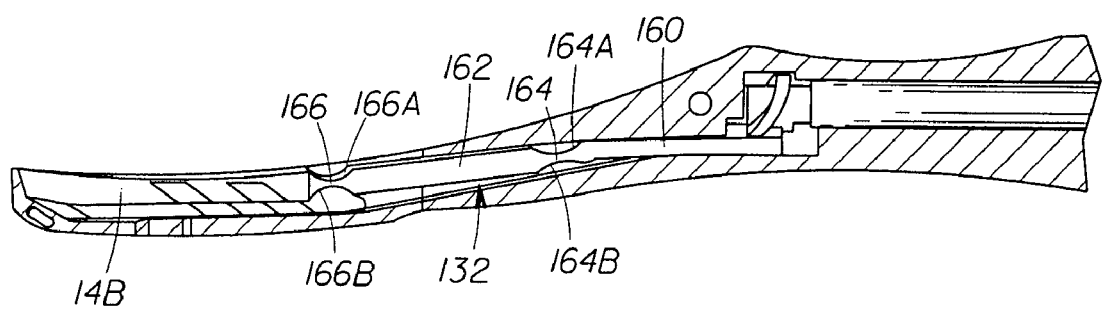
FIG. 9 is a partial cross-sectional side view of the toothbrush of FIG. 6 including an alternate drivetrain in accordance with the principles of the present disclosure.

As mentioned above, the drivetrain 32 depicted and described thus far may include a linear follower link 60 coupled to an articulation link 62 to drive the movable component 14B of the head 14. Such a configuration is merely one embodiment capable of accomplishing the principles of the present disclosure. FIG. 9 depicts an alternative embodiment including a drivetrain 332 constructed as a single unitary piece. Moreover, the drivetrain 332 and the movable component 14B of the head 14 may be constructed as a single, unitary piece, in some embodiments. As shown, the drivetrain 332 may include a linear follower portion 160, an articulation portion 162, a first elbow portion 164, and a second elbow portion 166. The first elbow portion 164 can be disposed between the linear follower link 160 and the articulation link 162. The second elbow portion 166 can be disposed between the articulation link 162 and the movable component 14B of the head 14.

The linear follower portion 160 and the articulation portion 162 are generally straight rigid members. The movable component 14B of the head 14 can be similar to that described above, with the exception of it being constructed integrally with the drivetrain 332. The first elbow portion 164 can be defined by opposing inwardly arched surfaces 164A, 164B. Similarly, the second elbow portion 166 can be defined by opposing inwardly arched surfaces 166A, 166B. Accordingly, the first and second elbow portions 164, 166 are flexible, thereby enabling the drivetrain 332 to pivot thereat and operate similarly to the drivetrain 32, 132, 232 described above with respect to FIGS. 1-7.

In light of the foregoing, it should be appreciated that the various components of the toothbrushes 10, 100, 200, 300 disclosed herein may be made of virtually any material. For example, in one form, the handle 12, 112, 212, the head 14, and the actuator assemblies 26, 126, 226 may all be constructed of a substantially rigid polymer. In another form, portions of the actuator assemblies 26, 126, 226 may be constructed of a metal such as aluminum or steel. In yet another form, the head 14 may be made of a polymer that is different from a polymer used to construct the handle 12, 112, 212 such as a flexible polymer to provide for a different level of comfort inside the user's mouth.

It should further be appreciated that while the present disclosure has included a head 14 of a toothbrush 10, 100, 200 having a fixed component 14A and a movable component 14B, an alternate form of the fixed component 14a may not actually be fixed. For example, the fixed component 14A may be constructed of a flexible material such as an elastomer that enables the fixed component 14A to slightly deflect or flex while the movable component 14B travels between the first and second positions. Such flexibility may be designed to reduce frictional wear between the fixed and movable components 14A, 14B, thereby prolonging the useful life of the toothbrush.

Furthermore, it should be appreciated that while the above-described head 14 of the toothbrushes 10, 100, 200, 300 have been depicted and described herein as including a fixed component 14A with sides 20 extending longitudinally along the outside of the movable component 14B, in an alternate form, the fixed and movable components 14A, 14B may be reversed. For example, the sides 20 of the fixed component 14A may be operably connected to the actuator assembly 26, 126, 226 and moveable between first and second positions relative to the movable component 14B. So configured, the fixed component 14A would actually be movable and the movable component would actually be fixed. Still further, it should be appreciated that while the movable component 14B has been disclosed as being moveable between a first position and a second position, an alternate form of the toothbrush may include the movable component 14B being moveable between a first, a second, and a third position, or any number of positions, thereby providing a head 14 capable of providing any number of configurations. In such a toothbrush 10, 100, 200, 300 the powered actuator assembly 26 may alternatingly displace the movable component 14B between, for example, the first and second positions, then the first and third positions, followed by the second and third positions, or any other sequence of positions that may be desirable for a particular cleaning operation.

Additionally, with reference to FIG. 4A, while the outer and inner bristle fields 16A, 16B have been disclosed herein as generally terminating at the same plane 92, 94 when the movable component 14B is in the first position, an alternate form may include the outer and inner bristle fields 16A, 16B terminating at different planes when the movable component 14B is in the first position. For example, the first plane 92 may be disposed slightly above or below the second plane 94 when the movable component 14A is in the first position.

Still further, while the fixed and movable components 14A, 14B of the head 14 have been disclosed herein as cooperating with each other via the slots 44 on the fixed component 14A and the bosses 52 on the movable component 14B, an alternate form of the invention may include the bosses 52 on the fixed component 14A and the slots 44 in the movable component 14B. In another form, the fixed and movable components 14A, 14B may not include slots 44 and bosses 52 at all, but rather slots and pins, or any other suitable surface or suitable device capable of guiding the two components relative to each other. Still further, the fixed and movable components 14A, 14B may cooperate without bosses 52 or pins and slots 44, but merely by sliding relative to one another. Finally, while the second position of the movable component 14B, which is illustrated in FIG. 4B, has been disclosed herein as being downward and to the right of the first position relative to the orientation of FIGS. 4A and 4B, an alternate form of the toothbrush 10, 100, 200 may include the second position being located only downward from the first position. A still further alternate form may include the second position located upward from the first position or in any other location relative to the first position.

Still yet, while the toothbrushes 10, 100, 200, 300 have been primarily disclosed as moving the movable component 14B between a first position, wherein the inner bristle field 16B occupies a second plane 94, and a second position, wherein the inner bristle field 16B occupies a third plane 96, an alternate form of the toothbrush 10, 100, 200, 300 may not move the inner bristle field 16B (or even the outer bristle field 16A) between two planes. For example, in one form, the inner bristle field 16B or the outer bristle field 16A may be pivoted between a first angular position relative to the head 14 and a second angular position relative to the head 14, wherein the subject bristle field 16A, 16B terminates within a fixed plane. So configured, the bristles 16 can occupy varying configurations, each aimed at optimizing a different cleaning function, without necessarily requiring the bristles 16 to be moved between multiple planes. In such embodiments, the angle between the bristles and the movable component 14B and/or the fixed component 14A may be adjusted to effect the first and/or the second configuration. Thus, it should be appreciated that the present disclosure is not limited to toothbrushes 10, 100, 200, 300 having bristles 16 moveable between various planes or various angles, but rather toothbrushes 10, 100, 200, 300 having bristles 16 moveable between any two or more configurations. Accordingly, it should be appreciated that the scope of the present disclosure is not limited to the forms of the toothbrush 10, 100, 200, 300 described herein, but rather, these are mere examples of what may be considered to be within the scope of the present invention.

Figure 10A:
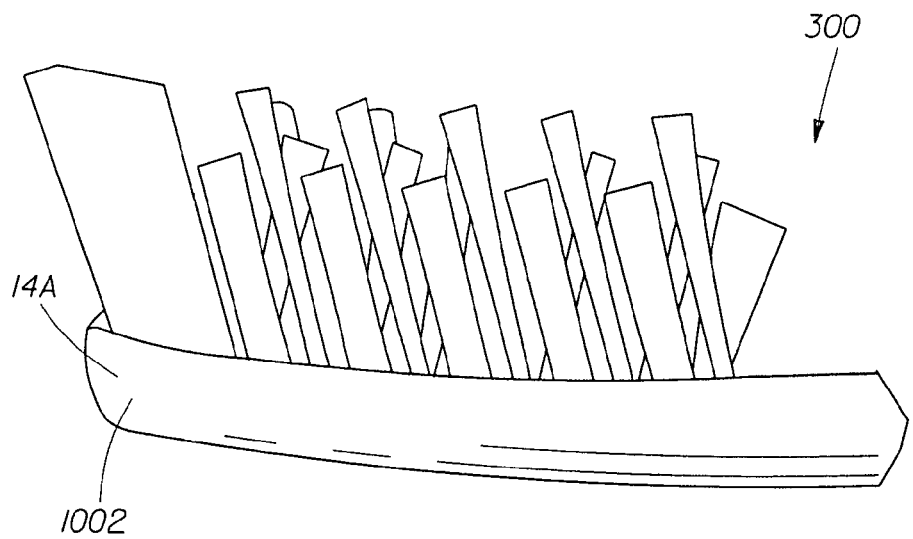
FIGS. 10A and 10B are elevation views showing a portion of a toothbrush constructed in accordance with the present invention.
Figure 10B:
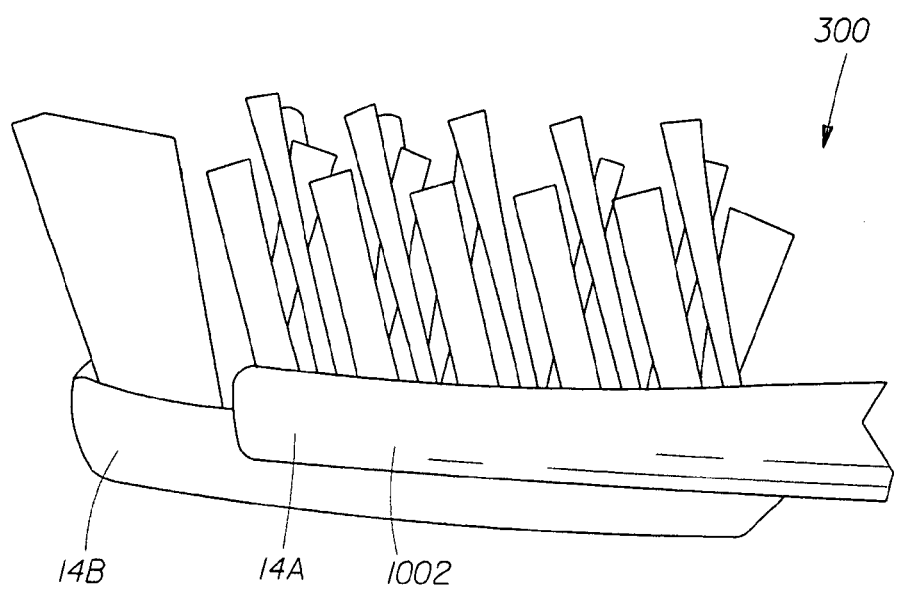

As discussed previously, with regard to FIG. 3, in some embodiments, the fixed component 14A may include a neck portion and a body portion having a base, a pair of sides, a toe, and inner side walls defining a recess in the fixed component. In contrast, embodiments are contemplated where the fixed component does not include a base and/or a toe. For example, as shown in FIGS. 10A and 10B, the fixed component 14A of the toothbrush 300 may comprise a pair of sides 1002. As described heretofore, the fixed component 14A and the movable component 14B may be configured such that the movable component 14B slidingly engages the fixed component 14A thereby allowing the movable component 14B to be adjustable between various configurations.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference, however the citation of any document is not construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. An oral hygiene device, comprising:
   a head having a fixed component, a movable component, and a linear slidable link engaging the movable component, the movable component being movable between a first and a second configuration;
   a first bristle field extending from the fixed component;
   a second bristle field extending from the movable component;
   a powered actuator for controllably moving the movable component between the first and second configurations;
   the linear slidable link being slidably movable, to position the movable component in a first plane in the first configuration and in a second plane in a second configuration, and wherein the second plane is disposed subjacent to the first plane.

2. The oral hygiene device of claim 1, wherein the second plane is disposed between 0 millimeters and 2 millimeters from the first plane.

3. The oral hygiene device of claim 1, wherein the powered actuator cycles the component between the first and second configurations, and wherein a time period between cycles is at least about 0.5 seconds.

4. The oral hygiene device of claim 1, wherein the fixed component comprises two rows of bristle tufts, wherein the movable component comprises at least one row of bristle tufts, and wherein the at least one row of bristle tufts is disposed between the two rows of bristle tufts.

5. The oral hygiene device of claim 1, further comprising a handle and a vibration device disposed within the handle.

6. The oral hygiene device of claim 1, further comprising an auxiliary bristle field extending from the fixed component.

7. The oral hygiene device of claim 1, further comprising an auxiliary bristle field extending from the movable component.

8. The oral hygiene device of claim 1, further comprising an auxiliary bristle field extending from the first head portion or from the second head portion.

9. A toothbrush having a handle, a head, and a neck extending between the handle and the head, the toothbrush further comprising:
   a first bristle field committed to a first tooth engaging position;
   a second bristle field extending from a movable component engaged with a
   a linear slidable link, the linear slidable link being slidably movable, to cycle the movable component and second bristle field extending therefrom between a second tooth engaging position and a third tooth engaging position, wherein the third tooth engaging position is subjacent to the first tooth engaging position; and
   a powered actuator for controllably moving the second bristle field between the second and third tooth engaging positions.

10. The oral hygiene device of claim 9, wherein the third tooth engaging position is disposed between 0 millimeters and 2 millimeters from the first tooth engaging position.

11. The oral hygiene device of claim 9, wherein the powered actuator cycles the second bristle field between the second and third tooth engaging positions, and wherein a time period between cycles is at least about 0.5 seconds.

12. The oral hygiene device of claim 9, wherein the first bristle field further comprises two rows of bristle tufts, wherein the second bristle field further comprises at least one row of bristle tufts, and wherein the at least one row of bristle tufts is disposed between the two rows of bristle tufts.

13. The oral hygiene device of claim 9, further comprising a handle and a vibration device disposed within the handle.

14. A toothbrush comprising:
   a head having a first head portion and a second head portion, the first head portion being fixed with respect to the head and the second head portion being movable between a first configuration and a second configuration;
   a first bristle field extending from the first head portion, the first bristle field terminating in a first plane; and
   a second bristle field extending from the second head portion, wherein the second head portion is engaged with a linear slidable link, the linear slidable link being slidably movable, to cycle the second head portion and second bristle field extending therefrom between the first configuration and second configuration, the second bristle field terminates in a second plane in the first configuration, wherein the first plane and the second plane being coplanar, wherein the second bristle field terminates in a third plane in the second configuration, and wherein the third plane is disposed subjacent to the first plane.

15. The oral hygiene device of claim 14, wherein the third plane is disposed between 0 millimeters and 2 millimeters from the first plane.

16. The oral hygiene device of claim 14, further comprising a powered actuator for controllably moving a second head portion between the first and second configurations.

17. The oral hygiene device of claim 14, wherein the first head portion comprises two rows of bristle tufts, wherein the second head portion comprises at least one row of bristle tufts, and wherein the at least one row of bristle tufts is disposed between the two rows of bristle tufts.

* * * * *